(12) United States Patent
Greenstein

(10) Patent No.: US 7,846,420 B2
(45) Date of Patent: Dec. 7, 2010

(54) *MYCOBACTERIUM AVIUM* SUBSPECIES *PARATUBERCULOSIS* VACCINES AND METHODS OF USING THE SAME

(76) Inventor: Robert J. Greenstein, 73 Windsor Rd., Tenafly, NJ (US) 07670-2615

( * ) Notice: Subject to any disclaimer, the term of this patent is extended or adjusted under 35 U.S.C. 154(b) by 0 days.

(21) Appl. No.: 12/108,144

(22) Filed: Apr. 23, 2008

(65) Prior Publication Data

US 2008/0260782 A1   Oct. 23, 2008

Related U.S. Application Data

(60) Provisional application No. 60/913,315, filed on Apr. 23, 2007.

(51) Int. Cl.
*A61K 49/00* (2006.01)
*A61K 39/02* (2006.01)
*A61K 39/04* (2006.01)

(52) U.S. Cl. ............... 424/9.2; 424/9.1; 424/184.1; 424/234.1; 424/248.1; 424/278.1; 435/41; 435/69.1; 435/243; 435/253.1

(58) Field of Classification Search .......... 424/9.1, 424/9.2, 184.1, 234.1, 248.1, 278.1; 435/41, 435/69.1, 243, 253.1
See application file for complete search history.

(56) References Cited

U.S. PATENT DOCUMENTS

| 6,156,322 | A | 12/2000 | Herman-Taylor | 424/248.1 |
| 2004/0234533 | A1* | 11/2004 | Aldwell et al. | 424/184.1 |
| 2004/0260078 | A1 | 12/2004 | Herman-Taylor | 536/23.1 |
| 2005/0025783 | A1* | 2/2005 | Murray et al. | 424/190.1 |
| 2005/0232937 | A1* | 10/2005 | Willemsen et al. | 424/190.1 |
| 2006/0204521 | A1 | 9/2006 | Herman-Taylor | 424/200.1 |

OTHER PUBLICATIONS

Webster's II, New Riverside University Dictionary, Houghton Mifflin Company, Boston, MA , p. 626, 1988.*
Dictionary of Microbiology and Molecular Biology, 2$^{nd}$ Edition, John Wiley & Sons, New York, NY, p. 452, 1987.*
Stedman's Medical Dictionary, 26$^{th}$ Edition, Williams & Wilkins, Baltimore MD, p. 868, 1995.*
Greenstein, Robert J., Lancet Infectious Diseases 2003 3:507-514.
Hermon-Taylor, J., Ital. J Gastroenterol Hepatol 1998 30:607-610.
Borody et al., Digest Liver Dis 2002 34:29-38.
Greenstein, R.J., Genetics, Barrier Function, immunologic & Microbial Pathways. Munster, Germany 2005: 25.
Naser et al., Lancet 2004 364:1039-1044.
Autschblach et al., GUT 1988 29:588-592.
Greenstein, R.J., Genetics, Barrier Function, immunologic & Microbial Pathways. Munster, Germany 2005: 24.
Greenstein, R.J. , Chron's and Colitis Foundation (CCFA) National Research and Clinical Conference. Fourth Annual Advances in Inflammatory Bowel Disease 2005 Miami, FL:211.
Greenstein et al., GUT 1988 29:588-592.
Gilberts et al., Proc. Natl. Acad. Sci. USA 1994 91(126) :12721-12724.
Greenstein & Collins Lancet 2004 364 (9432) : 396-397.
Hines et al., 8$^{th}$ International Colloquium on Paratuberculosis 2005, Copenhagen, Denmark pp. 54 and 105.
Uzonna et al., Proc. 75$^{th}$ International Colloquium on Paratuberculosis 2002 Bilbao, Spain:41.
Andersen at al., Infection and immunity 1991 59(6):1905-1910.
El-Zaatari et al., Current Microbiology 1994 29 : 177-184.
De Kessel et al., Scand. J. Immunol. 1992 36 : 201-212.
De Kessel et al., Journal of Clinical Microbiology 1993 31(4) :947-954.
Gilot et al., Journal of Bacteriology 1993 175 (15) : 4930-4935.
Silbaq et al., Infection and Immunity 1998 66(11):5576-5579.
Cameron et al., Microbiology 1994 140 : 1977-1982.
El-Zaatari et al., Journal of Clinical Microbiology 1997 35 (7) : 1794-1799.
El-Zaatari et al., Clinical and Diagnostic Laboratory Immunology 1995 2(6) :657-664.
Shinnick, Thomas M., Journal of Bacteriology 1987 169 (3) :1080-1088.
Thole et al., Infection and Immunity 1987 55 (6) :1466-1475.
Thole et al., Infection and Immunity 1988 56 (6) :1633-1640.
Olsen et al., Infection and Immunity 2000 68 (2) : 801-808.

* cited by examiner

*Primary Examiner*—Rodney P. Swartz
(74) *Attorney, Agent, or Firm*—Licata & Tyrrell P.C.

(57) ABSTRACT

The invention relates to vaccine compositions composed of at least one *Mycobacterium avium* subspecies *paratuberculosis* (MAP) antigen, or attenuated or killed MAP for use in methods of immunizing a human against a MAP infection, preventing or treating a MAP infection, and preventing a human disease associated with a MAP infection.

2 Claims, No Drawings

SEQUENCE LISTING

<160> NUMBER OF SEQ ID NOS: 7

<210> SEQ ID NO 1
<211> LENGTH: 100
<212> TYPE: PRT
<213> ORGANISM: Mycobacterium avium subsp. paratuberculosis

<400> SEQUENCE: 1

Met Ala Lys Val Asn Ile Lys Pro Leu Glu Asp Lys Ile Leu Val Gln
1               5                   10                  15

Ala Asn Glu Ala Glu Thr Thr Thr Ala Ser Gly Leu Val Ile Pro Asp
            20                  25                  30

Thr Ala Lys Glu Lys Pro Gln Glu Gly Thr Val Val Ala Val Gly Pro
        35                  40                  45

Gly Arg Trp Asp Asp Gly Ala Lys Arg Ile Pro Leu Asp Val Ser
    50                  55                  60

Glu Gly Asp Thr Val Ile Tyr Ser Lys Tyr Gly Gly Thr Glu Ile Lys
65                  70                  75                  80

Tyr Asn Gly Glu Glu Tyr Leu Ile Leu Ser Ala Arg Asp Val Leu Ala
                85                  90                  95

Val Val Ser Lys
            100

<210> SEQ ID NO 2
<211> LENGTH: 178
<212> TYPE: PRT
<213> ORGANISM: Mycobacterium avium subsp. paratuberculosis

<400> SEQUENCE: 2

Met Ser Val Glu Asn Leu Lys Glu Ala Leu Pro Glu Tyr Ala Lys Asp
1               5                   10                  15

Leu Lys Leu Asn Leu Gly Ser Ile Thr Arg Thr Thr Glu Leu Asn Glu
            20                  25                  30

Glu Gln Leu Trp Gly Thr Leu Leu Ala Ser Ala Ala Thr Arg Asn
        35                  40                  45

Thr Gln Val Leu Thr Glu Ile Gly Ala Glu Ala Asp Thr Leu Ser
    50                  55                  60

Ala Glu Ala Tyr His Ala Ala Leu Gly Ala Ala Ser Val Met Ala Met
65                  70                  75                  80

Asn Asn Val Phe Tyr Arg Gly Arg Gly Phe Leu Asp Gly Lys Tyr Asp
                85                  90                  95

Asp Leu Arg Ala Gly Leu Arg Met Asn Ile Ile Gly Asn Pro Gly Val
            100                 105                 110

Glu Lys Ala Asn Phe Glu Leu Trp Cys Phe Ala Val Ser Ala Ile Asn
        115                 120                 125

Gly Cys Pro Asp Cys Val Ala Ser His Glu His Thr Leu Arg Glu Ala
    130                 135                 140

Gly Val Ser Arg Glu Thr Ile Gln Glu Ala Leu Lys Ala Ala Ala Ile
145                 150                 155                 160

Ile Ser Gly Val Ala Gln Ala Ile Val Ala Ser Gln Thr Leu Ala Thr
                165                 170                 175

Ala Gly

<210> SEQ ID NO 3
<211> LENGTH: 298

```
<212> TYPE: PRT
<213> ORGANISM: Mycobacterium avium subsp. paratuberculosis

<400> SEQUENCE: 3

Met Thr Tyr Ser Pro Gly Ser Pro Gly Tyr Pro Ala Gln Ser Gly
1               5                   10                  15

Gly Thr Tyr Ala Gly Ala Thr Pro Ser Phe Ala Lys Asp Asp Gly
                20                  25                  30

Lys Ser Lys Leu Pro Leu Tyr Leu Asn Ile Ala Val Ala Leu Gly
            35                  40                  45

Phe Ala Ala Tyr Leu Leu Asn Phe Gly Pro Thr Phe Thr Ile Gly Ala
50                  55                  60

Asp Leu Gly Pro Gly Ile Gly Gly Arg Ala Gly Asp Ala Gly Thr Ala
65                  70                  75                  80

Val Val Val Ala Leu Leu Ala Ala Leu Leu Ala Gly Leu Gly Leu Leu
                85                  90                  95

Pro Lys Ala Lys Ser Tyr Val Gly Val Ala Val Val Ala Val Leu
                100                 105                 110

Ala Ala Leu Leu Ala Ile Thr Glu Thr Ile Asn Leu Pro Ala Gly Phe
                115                 120                 125

Ala Ile Gly Trp Ala Met Trp Pro Leu Val Ala Cys Val Val Leu Gln
130                 135                 140

Ala Ile Ala Ala Val Val Val Leu Leu Asp Ala Gly Val Ile Thr
145                 150                 155                 160

Ala Pro Ala Pro Arg Pro Lys Tyr Asp Pro Tyr Ala Gln Tyr Gly Gln
                165                 170                 175

Tyr Gly Gln Tyr Gly Gln Tyr Gly Gln Gln Pro Tyr Tyr Gly Gln Pro
                180                 185                 190

Gly Gly Gln Pro Gly Gly Gln Pro Gly Gly Gln Gln His Ser Pro Gln
                195                 200                 205

Gly Tyr Gly Ser Gln Tyr Gly Tyr Gly Gln Gly Ala Pro Thr
                210                 215                 220

Gly Gly Phe Gly Ala Gln Pro Ser Pro Gln Ser Gly Pro Gln Gln Ser
225                 230                 235                 240

Ala Gln Gln Gln Gly Pro Ser Thr Pro Thr Gly Phe Pro Ser Phe
                245                 250                 255

Ser Pro Pro Pro Asn Val Gly Gly Ser Asp Ser Gly Ser Ala Thr
                260                 265                 270

Ala Asn Tyr Ser Glu Gln Ala Gly Gly Gln Gln Ser Tyr Gly Gln Glu
                275                 280                 285

Pro Ser Ser Pro Ser Gly Pro Thr Pro Ala
    290                 295

<210> SEQ ID NO 4
<211> LENGTH: 361
<212> TYPE: PRT
<213> ORGANISM: Mycobacterium avium subsp. paratuberculosis

<400> SEQUENCE: 4

Met Ser Lys Ser His His His Arg Ser Val Trp Trp Ser Trp Leu Val
1               5                   10                  15

Gly Val Leu Thr Val Val Gly Leu Gly Leu Gly Leu Gly Ser Gly Val
                20                  25                  30

Gly Leu Ala Pro Ala Ser Ala Ala Pro Ser Gly Leu Ala Leu Asp Arg
            35                  40                  45
```

```
Phe Ala Asp Arg Pro Leu Ala Pro Ile Asp Pro Ser Ala Met Val Gly
    50                  55                  60

Gln Val Gly Pro Gln Val Val Asn Ile Asp Thr Lys Phe Gly Tyr Asn
65                  70                  75                  80

Asn Ala Val Gly Ala Gly Thr Gly Ile Val Ile Asp Pro Asn Gly Val
                85                  90                  95

Val Leu Thr Asn Asn His Val Ile Ser Gly Ala Thr Glu Ile Ser Ala
            100                 105                 110

Phe Asp Val Gly Asn Gly Gln Thr Tyr Ala Val Asp Val Gly Tyr
        115                 120                 125

Asp Arg Thr Gln Asp Ile Ala Val Leu Gln Leu Arg Gly Ala Ala Gly
    130                 135                 140

Leu Pro Thr Ala Thr Ile Gly Glu Ala Thr Val Gly Glu Pro Ile
145                 150                 155                 160

Val Ala Leu Gly Asn Val Gly Gly Gln Gly Thr Pro Asn Ala Val
                165                 170                 175

Ala Gly Lys Val Val Ala Leu Asn Gln Ser Val Ser Ala Thr Asp Thr
            180                 185                 190

Leu Thr Gly Ala Gln Glu Asn Leu Gly Gly Leu Ile Gln Ala Asp Ala
    195                 200                 205

Pro Ile Lys Pro Gly Asp Ser Gly Gly Pro Met Val Asn Ser Ala Gly
210                 215                 220

Gln Val Ile Gly Val Asp Thr Ala Ala Thr Asp Ser Tyr Lys Met Ser
225                 230                 235                 240

Gly Gly Gln Gly Phe Ala Ile Pro Ile Gly Arg Ala Met Ala Val Ala
                245                 250                 255

Asn Gln Ile Arg Ser Gly Ala Gly Ser Asn Thr Val His Ile Gly Pro
            260                 265                 270

Thr Ala Phe Leu Gly Leu Gly Val Thr Asp Asn Asn Gly Asn Gly Ala
    275                 280                 285

Arg Val Gln Arg Val Val Asn Thr Gly Pro Ala Ala Ala Gly Ile
    290                 295                 300

Ala Pro Gly Asp Val Ile Thr Gly Val Asp Thr Val Pro Ile Asn Gly
305                 310                 315                 320

Ala Thr Ser Met Thr Glu Val Leu Val Pro His His Pro Gly Asp Thr
                325                 330                 335

Ile Ala Val His Phe Arg Ser Val Asp Gly Gly Glu Arg Thr Ala Asn
            340                 345                 350

Ile Thr Leu Ala Glu Gly Pro Pro Ala
    355                 360

<210> SEQ ID NO 5
<211> LENGTH: 319
<212> TYPE: PRT
<213> ORGANISM: Mycobacterium avium subsp. paratuberculosis
<220> FEATURE:
<221> NAME/KEY: misc_feature
<222> LOCATION: (67)..(67)
<223> OTHER INFORMATION: Xaa can be any naturally occurring amino acid

<400> SEQUENCE: 5

Met Pro Ser Ala Ala Ser Thr Ser Ala Ala Pro Pro Ser His Arg Ala
1               5                   10                  15

Ala Leu Ser Ala Ala Ala Gly Pro Pro Gly Cys Trp Trp Pro Ala Ala
                20                  25                  30

Gly Arg Arg Gln Gly Glu Arg Arg Gly Arg Val Leu Gly Leu Ala Ala
```

-continued

```
                35                  40                  45
Val Gly Gln Arg Trp Leu Ile Pro Leu Asp His Gly Ala Val Gly Val
 50                  55                  60
Gly Leu Xaa Gly Arg Lys Ala Asp Gly Val Gly Val Gly Gln Leu His
 65                  70                  75                  80
Arg Gln Pro Glu Gln Gly Glu Leu Val Gly Pro Asp Ala Ala Arg
                 85                  90                  95
Gly Gly Ser Gln Val Thr Glu Arg Thr Val Pro Asp Ala Ala Ser Arg
                100                 105                 110
Ser Ser Arg Ala Val Gln Pro Gly Met Val Ser Val Cys Ala Ala Ala
                115                 120                 125
Thr Leu Gly Ser Ala Thr Val Ser Ala Val Val Ala Ala Pro Val Phe
130                 135                 140
Asp Ser Leu Gly Thr Trp Lys Val Thr Thr Ala Met Ala Pro Arg Thr
145                 150                 155                 160
Gly Leu Ser Leu Pro Ala Cys Thr Cys Ala Asp Ala Ile Gly Asp Gln
                165                 170                 175
Ala Thr Asp Pro Arg His Arg Ala Ala Thr Ala Thr Ser Arg Arg Gly
                180                 185                 190
Ala Arg Arg Leu Arg Gly Gly Met Arg Val Ala Gln Pro Glu Ala Gly
                195                 200                 205
His Gln Val Arg Leu Asp Ala Val Glu Leu Arg Gly Asp Gly Val
                210                 215                 220
Ser Arg Pro Ala Pro Gly Gly His Val Leu Arg Gly Gly His Arg
225                 230                 235                 240
Gly Arg Gln Val Gly Glu Pro Leu Gly Asp Gly Gly Asp Glu Leu Leu
                245                 250                 255
Gly Leu Ala Val Leu Gly Leu Arg Ser Cys Thr Ser Arg Asn Asp Phe
                260                 265                 270
Ser Ala Pro Ala Met Arg Ala Asp Ser Trp Ala Pro Trp Pro Glu Asn
                275                 280                 285
Trp Pro Ile Trp Ala Asn Gly Thr Pro Ser Arg Ser Ala Arg Arg Trp
                290                 295                 300
Ser Ile Ser Ala Arg Ala Glu Thr Gly Arg Gly Arg Thr Gly
305                 310                 315

<210> SEQ ID NO 6
<211> LENGTH: 195
<212> TYPE: PRT
<213> ORGANISM: Mycobacterium avium subsp. paratuberculosis

<400> SEQUENCE: 6

Met Pro Leu Leu Thr Ile Gly Asp Gln Phe Pro Ala Tyr Glu Leu Thr
 1                   5                  10                  15
Ala Leu Ile Ala Gly Asp Leu Ser Lys Val Asp Ala Lys Gln Pro Gly
                 20                  25                  30
Asp Tyr Phe Thr Thr Val Thr Ser Glu Asp His Ala Gly Lys Trp Arg
                 35                  40                  45
Val Val Phe Phe Trp Pro Lys Asp Phe Thr Phe Val Cys Pro Thr Glu
 50                  55                  60
Ile Ala Thr Phe Gly Lys Leu Asn Asp Glu Phe Glu Asp Arg Asp Ala
 65                  70                  75                  80
Gln Val Leu Gly Val Ser Ile Asp Ser Glu Phe Val His Phe Asn Trp
                 85                  90                  95
```

```
Arg Ala Gln His Glu Asp Leu Lys Asn Leu Pro Phe Pro Met Leu Ser
            100                 105                 110

Asp Ile Lys Arg Glu Leu Ser Leu Ala Thr Gly Val Leu Asn Ala Asp
            115                 120                 125

Gly Val Ala Asp Arg Ala Thr Phe Ile Val Asp Pro Asn Asn Glu Ile
            130                 135                 140

Gln Phe Val Ser Val Thr Ala Gly Ser Val Gly Arg Asn Val Glu Glu
145                 150                 155                 160

Val Leu Arg Val Leu Asp Ala Leu Gln Ser Asp Glu Leu Cys Ala Cys
            165                 170                 175

Asn Trp Arg Lys Gly Asp Pro Thr Leu Asn Ala Thr Glu Leu Leu Lys
            180                 185                 190

Ala Ser Ala
        195

<210> SEQ ID NO 7
<211> LENGTH: 582
<212> TYPE: PRT
<213> ORGANISM: Mycobacterium avium subsp. paratuberculosis

<400> SEQUENCE: 7

Met Leu Gly Arg Asp Gly Glu Ala Arg Leu Cys Arg Arg Pro Thr Ala
1               5                   10                  15

Ala Ala Trp Ser Ser Val Ala Gly Thr Ala Pro Gly Gln Asp Val Ser
            20                  25                  30

Ser Pro Ile Arg Arg Asn His Phe Ala Met Ala Lys Thr Ile Ala Tyr
            35                  40                  45

Asp Glu Glu Ala Arg Arg Gly Leu Glu Arg Gly Leu Asn Ala Leu Ala
            50                  55                  60

Asp Ala Val Lys Val Thr Leu Gly Pro Lys Gly Arg Asn Val Val Leu
65                  70                  75                  80

Glu Lys Lys Trp Gly Ser Pro Thr Ile Thr Asn Asp Gly Val Ser Ile
            85                  90                  95

Ala Lys Glu Ile Glu Leu Glu Asp Pro Tyr Glu Lys Ile Gly Ala Glu
            100                 105                 110

Leu Val Lys Glu Val Ala Lys Lys Thr Asp Asp Val Ala Gly Asp Gly
            115                 120                 125

Thr Thr Thr Ala Thr Val Leu Ala Gln Ala Leu Val Arg Glu Gly Leu
            130                 135                 140

Arg Asn Val Ala Ala Gly Ala Asn Pro Leu Gly Leu Lys Arg Gly Ile
145                 150                 155                 160

Glu Lys Ala Val Glu Lys Val Thr Glu Thr Leu Leu Lys Ser Ala Lys
            165                 170                 175

Glu Val Glu Thr Lys Asp Gln Ile Ala Ala Thr Ala Ala Ile Ser Ala
            180                 185                 190

Gly Asp Gln Ser Ile Gly Asp Leu Ile Ala Glu Ala Met Asp Lys Val
            195                 200                 205

Gly Asn Glu Gly Val Ile Thr Val Glu Glu Ser Asn Thr Phe Gly Leu
            210                 215                 220

Gln Leu Glu Leu Thr Glu Gly Met Arg Phe Asp Lys Gly Tyr Ile Ser
225                 230                 235                 240

Gly Tyr Phe Val Thr Asp Ala Glu Arg Gln Glu Ala Val Leu Glu Asp
            245                 250                 255

Pro Phe Ile Leu Leu Val Ser Ser Lys Val Ser Thr Val Lys Asp Leu
            260                 265                 270
```

-continued

```
Leu Pro Leu Leu Glu Lys Val Ile Gln Ala Gly Lys Pro Leu Leu Ile
        275                 280                 285
Ile Ala Glu Asp Val Glu Gly Glu Ala Leu Ser Thr Leu Val Val Asn
        290                 295                 300
Lys Ile Arg Gly Thr Phe Lys Ser Val Ala Val Lys Ala Pro Gly Phe
305                 310                 315                 320
Gly Asp Arg Arg Lys Ala Met Leu Gln Asp Met Ala Ile Leu Thr Gly
                325                 330                 335
Gly Gln Val Ile Ser Glu Glu Val Gly Leu Ser Leu Glu Ser Ala Asp
                340                 345                 350
Ile Ser Leu Leu Gly Lys Ala Arg Lys Val Val Val Thr Lys Asp Glu
        355                 360                 365
Thr Thr Ile Val Glu Gly Ala Gly Asp Ser Asp Ala Ile Ala Gly Arg
        370                 375                 380
Val Ala Gln Ile Arg Thr Glu Ile Glu Asn Ser Asp Ser Asp Tyr Asp
385                 390                 395                 400
Arg Glu Lys Leu Gln Glu Arg Leu Ala Lys Leu Ala Gly Gly Val Ala
                405                 410                 415
Val Ile Lys Ala Gly Ala Ala Thr Glu Val Glu Leu Lys Glu Arg Lys
                420                 425                 430
His Arg Ile Glu Asp Ala Val Arg Asn Ala Lys Ala Ala Val Glu Glu
        435                 440                 445
Gly Ile Val Ala Gly Gly Val Ala Leu Leu His Ala Ile Pro Ala
        450                 455                 460
Leu Asp Glu Leu Lys Leu Glu Gly Glu Glu Ala Thr Gly Ala Asn Ile
465                 470                 475                 480
Val Arg Val Ala Leu Glu Arg Pro Leu Lys Gln Ile Ala Phe Asn Gly
                485                 490                 495
Gly Leu Glu Pro Gly Val Val Ala Glu Lys Val Arg Asn Ser Pro Ala
                500                 505                 510
Gly Thr Gly Leu Asn Ala Ala Thr Gly Lys Tyr Glu Asp Leu Leu Lys
        515                 520                 525
Ala Gly Ile Thr Glu Pro Val Lys Val Thr Arg Ser Ala Leu Gln Asn
        530                 535                 540
Ala Ala Ser Ile Ser Gly Leu Phe Leu Thr Thr Glu Ala Val Val Ala
545                 550                 555                 560
Asp Lys Pro Glu Lys Thr Ala Pro Pro Ala Gly Asp Pro Thr Gly Gly
                565                 570                 575
Met Gly Gly Met Asp Phe
                580
```

MYCOBACTERIUM AVIUM SUBSPECIES PARATUBERCULOSIS VACCINES AND METHODS OF USING THE SAME

INTRODUCTION

This application claims benefit of priority to U.S. Provisional Patent Application Ser. No. 60/913,315, filed Apr. 23, 2007, the content of which is incorporated herein by reference in its entirety.

BACKGROUND OF THE INVENTION

Johne's disease is a chronic diarrheal enteric disease in ruminants that is caused by *Mycobacterium avium* subspecies *paratuberculosis* (MAP)(Johne & Frothingham (1895) *Dtsch. Zeitschr. Tiermed. Vergl. Pathol.* 21:438-454). Live MAP is shed into the milk of cows with Johne's disease (Sweeney (1996) *Vet. Clin. North Am. Food Anim. Pract.* 12(2):305-12). MAP has been cultured from commercially available pasteurized milk in Europe and the United States (Grant (1998) *Appl. Environ. Microbiol.* 64(7):2760-1; Ellingson, et al. (2005) *J. Food Prot.* 68(5):966-72). When Crohn's disease was first described (Crohn, et al. (1932) *J. Amer. Med. Assoc.* 99:1323-1328), similarities to Johne's disease were identified (Dalziel (1913) *Br. Med. J.* ii:1068-1070). However, in humans MAP exists in the cell wall-deficient form (Chiodini (1987) *J. Clin. Microbiol.* 25:796-801). Therefore, in the early analysis of Crohn's disease, MAP could not be detected in humans by the mycobacterial identification techniques of the time, because such techniques stained the mycobacterial cell wall (Ziehl (1882) *Dtsch. Med. Wschr.* 8:451; Neelsen (1883) *Zbl. Med. Wiss.* 21:497-501). However, since 1913 the presence of MAP has been identified in humans by other means (see, e.g., Greenstein (2003) *Lancet Infect. Dis.* 3(8):507-14) and an infectious etiology has been posited for some (Hermon-Taylor (1998) *Ital. J. Gastroenterol. Hepatol.* 30(6):607-10; Borody, et al. (2002) *Dig. Liver Dis.* 34(1):29-38), or all (Greenstein (2005) Genetics, Barrier Function, Immunologic & Microbial Pathways. Munster, Germany:25) of inflammatory bowel disease (IBD).

Since the first detection of MAP RNA (Mishina, et al. (1996) *Proc. Natl. Acad. Sci. USA* 93(18):9816-9820), MAP has been suggested as being the primary and unique, etiological agent of all IBD (Naser, et al. (2004) *Lancet* 364(9439):1039-1044; Autschbach, et al. (2005) *Gut* 54(7):944-9; Greenstein (2005) supra; Greenstein (2005) Genetics, Barrier Function, Immunologic & Microbial Pathways. Munster, Germany:24; Greenstein (2005) Crohn's and Colitis Foundation (CCFA) National Research and Clinical Conference. Fourth Annual Advances in Inflammatory Bowel Disease. Miami, Fla.:211) including Perforating and Non-perforating Crohn's disease (Greenstein, et al. (1988) *GUT* 29:588-592; Gilberts, et al. (1994) *Proc. Natl. Acad. Sci. USA* 91(126):12721-12724) and ulcerative colitis. It is believed that the particular clinical presentation of IBD that manifests is dependent upon the infected individual's immune response to MAP (Gilberts, et al. (1994) supra). This is analogous to another mycobacterial disease, leprosy. There are two clinical forms of leprosy, tuberculoid and lepromatous (Hansen (1874) *Norsk Magazin Laegevidenskaben* 4:1-88), both of which are caused by the same organism, *M. leprae*. The form of leprosy that manifests in a given individual is determined by the immune response of the infected patient (Yamamura, et al. (1991) *Science* 254:277-279), not by the phenotype or genotype of the leprosy bacillus.

It has been suggested that Koch's postulates (Koch (1882) *Berl. Klin. Wschr.* 19:221-230), originally promulgated for use in demonstrating tuberculosis infection, may have been met for MAP in Crohn's disease (Greenstein (2003) supra) and more recently for MAP in ulcerative colitis (Greenstein (2005) supra; Naser, et al. (2004) supra).

The link between MAP infection and other diseases is under investigation. An association between ulcerative colitis and Multiple Sclerosis has been suggested (Rang, et al. (1982) *The Lancet* pg. 555) and the positive association between IBD incidence rates and Multiple Sclerosis has led to the suggestion that these two chronic, immunologically-mediated diseases may have a common environmental etiology (Green, et al. (2006) *Am. J. Epidemiol.* 164(7):615-23). However, the common causal agent of ulcerative colitis and Multiple Sclerosis was not identified. Moreover, while the symptoms of Multiple Sclerosis have been ameliorated with variety of therapeutic agents including azathioprine, methotrexate, cyclophosphamide and mitoxantrone (Kaffaroni, et al. (2006) *Neurol. Sci.* 27 Suppl. 1:S13-7), which have been suggested to mediate the secondary inflammatory response, there has been no indication that these agents affect the primary etiological agent.

There is increasingly compelling evidence that MAP may be zoonotic (Greenstein & Collins (2004) *Lancet* 364(9432):396-7) and a human pathogen in gastrointestinal disease (Greenstein (2005) supra) and other diseases as well. There is an additional indication that in man, MAP is systemic and not confined to the gastrointestinal tract (Naser, et al. (2000) *Am. J. Gastroenterol.* 95(4):1094-5; Naser, et al. (2004) *Lancet* 364(9439):1039-1044). It is suggested that the reason MAP is zoonotic and has been missed as an etiological agent is that the medical profession has been unknowingly treating MAP with anti-inflammatory agents (e.g., 5-amino salicylic acid, methotrexate, and 6-mercaptopurine), which in fact have anti-MAP activity (Greenstein, et al. (2007) *PLoS ONE* 2:e161; Greenstein, et al. American Society of Microbiology 2007, Toronto, Canada).

Given this identified association between MAP as the etiological agent for a variety of human diseases, there is a need in the art for compositions and methods for preventing MAP infection. The present invention meets this need by providing vaccines for the prevention of a MAP infection and MAP-associated diseases.

SUMMARY OF THE INVENTION

The present invention is a method for producing a vaccine for immunizing a human against a *Mycobacterium avium* subspecies *paratuberculosis* (MAP) infection. The method involves admixing at least one MAP antigen, or attenuated or killed MAP with a suitable carrier thereby producing a vaccine for the immunization of a human against a MAP infection. In one embodiment, the attenuated or killed MAP is cell wall-competent or cell wall-deficient. In another embodiment, the MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, AhpC antigen or 65 kDa antigen.

Methods for immunizing a human against a MAP infection, preventing or treating a MAP infection, and preventing a human disease associated with a MAP infection are also provided.

DETAILED DESCRIPTION OF THE INVENTION

Epidemiological analysis identifies a parallelism in the increasing incidence of Crohn's disease, ulcerative colitis and Multiple Sclerosis (Green, et al. (2006) supra). In Alzheimer's disease the use of "anti-inflammatories" shows therapeutic benefit (Rogers, et al. (1993) *Neurology* 43(8):1609-11). Additionally, there is the suggestion that rheumatoid arthritis is protective against Alzheimer's disease (McGeer, et al. (1990) *Lancet* 335(8696):1037). Analogous to lepromatous leprosy (Hansen (1874) *Norsk Magazin for Laegevidenskaben* 4:1-88) and tuberculoid leprosy, it is now posited that Multiple Sclerosis and perforating Crohn's disease (Gilberts, et al. (1994) *Proc. Natl. Acad. Sci. USA* 91(126):12721-12724) are the "acute" forms of a *Mycobacterium avium* subspecies *paratuberculosis* (MAP; basonym *M. paratuberculosis*) infection, whereas Alzheimer's Disease and obstructive Crohn's or ulcerative colitis are the chronic forms of a MAP infection. It is further posited that a causative relationship between MAP and diseases such as IBD and Multiple Sclerosis have been missed because it has not been appreciated that standard "immunomodulatory" treatment regimes, whose mechanisms of actions are unknown or speculated upon, are in fact effective because they are treating a MAP infection. It is posited that MAP is also responsible for a variety of diseases where an infectious etiology has been suggested, e.g., sarcoidosis, ankylosing spondylitis, psoriasis, and psoriatic arthritis and rheumatoid arthritis. Coincidentally, these diseases are often treated with "immunomodulatory" and "anti-inflammatory" agents that have now been shown to interfere with the growth kinetics of MAP.

While some reports have indicated that high-temperature short-time pasteurization does not effectively kill MAP in milk (Grant, et al. (1998) *Lett. Appl. Microbiol.* 26:166-170; Grant, et al. (1999) *Lett. Appl. Microbiol.* 28:461-465), killing by turbulent-flow conditions has been demonstrated (Stabel, et al. (1997) *Appl. Environ. Microbiol.* 63:4975-4977). Given the identification of potential sources of infection and that MAP is widespread over the industrialized as well as non-industrialized world and, a multipronged approach including vaccines, antibiotics, and public health measures are needed to control and prevent MAP infections. Accordingly, having appreciated that MAP may be the etiological agent of a plurality of human diseases or conditions, the present invention provides vaccines and methods for immunizing human subjects against a MAP infection.

For the purposes of the present invention, a vaccine of the present invention is intended to include whole MAP cells, either cell wall-competent or cell wall-deficient; MAP cell extracts; isolated protein (i.e., a subunit vaccine); or combinations thereof.

Whole cell vaccines can be produced from cell wall-competent and/or cell wall-deficient MAP which has been inactivated or attenuated or has been killed. Live attenuated vaccines have the advantage of mimicking the natural infection enough to trigger an immune response similar to the response to the wild-type organism. Such vaccines generally provide a high level of protection, especially if administered by a natural route, and some may only require one dose to confer immunity. Because MAP exists in humans in the cell wall-deficient state, a vaccine which targets this obligate intracellular form is desirable. By way of illustration, cell wall-competent and cell wall-deficient (i.e., spheroplasts) vaccine preparations have been shown to reduce lesion scores associated with Johne's Disease in baby goats (Hines, et al. (2005) *8th International Colloquium on Paratuberculosis*, Copenhagen, Denmark). MAP can be attenuated using any conventional strategy employed in producing an attenuated M. tuberculosis. For example, serial passage or culture of the active organism in culture media or cells can be employed to attenuate MAP. Alternatively, the vaccine of the present invention can contain heat-killed MAP cells. In this regard, vaccination of calves with a heat-killed field strain of MAP results in high concentrations of IFN-γ and better protection against a MAP challenge exposure than does a commercially available vaccine (Uzonna, et al. (2002) *Proc. 7th Intl. Coll. Paratuberculosis*; Juste (ed)).

In addition, or as an alternative to an attenuated or killed MAP vaccine, a MAP subunit vaccine can be employed. Any one of the well-known MAP-specific antigens, or antigen fragments thereof, commonly employed in veterinary medicine can be used as a vaccine in accordance with the present invention. See Table 1.

TABLE 1

| MAP protein | Characteristic | Size (kDa) | SEQ ID NO: |
|---|---|---|---|
| GroES | Heat shock protein | 10 | 1 |
| AhpD | Alkyl hydroperoxide reductase D | 19 | 2 |
| 32-kDa antigen | Fibronectin binding properties, secreted | 32 | |
| 34-kDa antigen | Cell wall antigen, B-cell epitope | 34 | 3 |
| 34-kDa antigen | Serine protease | 34 | 4 |
| 34.5-kDa antigen | Cytoplasmic protein | 34.5 | |
| 35-kDa antigen | Immunodominant protein | 35 | |
| 36-kDa antigen | p36 antigen | 36 | 5 |
| 42-kDa antigen | Cytoplasmic protein | 42 | |
| 44.3-kDa antigen | Soluble protein | 44.3 | |
| AhpC | Alkyl hydroperoxide reductase C | 45 | 6 |
| 65-kDa antigen | GroEL heat shock protein | 65 | 7 |

The 32-kDa secreted protein with fibronectin binding properties has been implicated in protective immunity (Andersen, et al. (1991) *Infect. Immun.* 59:1905-1910; El-Zaatari, et al. (1994) *Curr. Microbiol.* 29:177-184) and the 34-kDa cell wall antigenic protein is homologous to a similar immunogenic protein in *M. leprae* (De Kesel, et al. (1992) *Scand. J. Immunol.* 36:201-212; De Kesel, et al. (1993) *J. Clin. Microbiol.* 31:947-954; Gilot, et al. (1993) *J. Bacteriol.* 175:4930-4935; Silbaq, et al. (1998) *Infect. Immun.* 66:5576-5579). The seroreactive 34-kDa serine protease expressed in vivo by MAP has also been described (Cameron, et al. (1994) *Microbiology* 140:1977-1982; however, this antigen is different from the 34-kDa antigen described above. Another strongly immunoreactive protein of 35 kDa has also been identified in *M. avium* complex isolates, including MAP (El-Zaatari, et al. (1997) *J. Clin. Microbiol.* 35:1794-1799). A more thoroughly characterized protein of 65 kDa from MAP is a member of the GroEL family of heat shock proteins (El-Zaatari, et al. (1994) *Curr. Microbiol.* 29:177-184; El-Zaatari, et al. (1995) *Clin. Diagn. Lab. Immunol.* 2:657-664). Like the GroES proteins, the GroEL antigens from other mycobacteria are highly immunogenic (Shinnick (1987) *J. Bacteriol.* 169:1080-1088; Thole, et al. (1987) *Infect. Immun.* 55:1466-1475; Thole, et al. (1988) *Infect. Immun.* 56:1633-1640).

The alkyl hydroperoxide reductases C and D (AhpC and AhpD) have also been characterized as immunogenic proteins of MAP (Olsen, et al. (2000) *Infect. Immun.* 68:801-808). Unlike other mycobacteria, large amounts of these antigens are produced by MAP when the bacilli are grown without exposure to oxidative stress. AhpC is the larger of the two proteins and appears to exist as a homodimer in its native form since it migrates at both 45 and 24 kDa under denaturing conditions. In contrast, AhpD is a smaller monomer, with a molecular mass of about 19 kDa. Antiserum from rabbits immunized against AhpC and AhpD reacted only with MAP proteins and not with proteins from other mycobacterial species, indicating that antibodies against these proteins are not cross-reactive. Furthermore, peripheral blood monocytes from goats experimentally infected with MAP were capable of inducing gamma interferon (IFN-γ) responses after stimulation with AhpC and AhpD, confirming their immunogenicity (Olsen, et al. (2000) *Infect. Immun.* 68:801-808).

Antigenic proteins disclosed herein, can be prepared and purified by any conventional method including recombinant production. The term purified does not require absolute purity; rather, it is intended as a relative definition, and can include preparations that are highly purified or preparations that are only partially purified.

Vaccines of the present invention are prepared using routine methods. Generally, vaccines are prepared as injectables, in the form of aqueous solutions or suspensions. Vaccines in an oil base are also well-known such as for inhaling. Solid forms which are dissolved or suspended prior to use can also be formulated. Suitable carriers, diluents and excipients are generally added that are compatible with the active ingredients and acceptable for use in humans. Examples of such carriers include, but are not limited to, water, saline solutions, dextrose, or glycerol. Carriers can also include liposomes or microspheres. Combinations of carriers can also be used. A generally recognized compendium of methods and ingredients of vaccine compositions is Remington: The Science and Practice of Pharmacy, Alfonso R. Gennaro, editor, 20th ed. Lippincott Williams & Wilkins: Philadelphia, Pa., 2000.

Vaccine compositions can further incorporate additional substances to stabilize pH, or to function as adjuvants, wetting agents, or emulsifying agents, which can serve to improve the effectiveness of the vaccine. Examples of suitable adjuvants include, but are not limited to, aluminum salts; Incomplete Freund's adjuvant; threonyl and n-butyl derivatives of muramyl dipeptide; lipophilic derivatives of muramyl tripeptide; monophosphoryl lipid A; 3'-de-O-acetylated monophosphoryl lipid A; cholera toxin; QS21; phosphorothionated oligodeoxynucleotides with CpG motifs and adjuvants disclosed in U.S. Pat. No. 6,558,670.

Vaccines are generally formulated for parenteral administration and are injected either subcutaneously or intramuscularly. Vaccines can also be formulated as suppositories or for oral or nasal administration using methods known in the art. The amount of vaccine sufficient to confer immunity to pathogenic MAP is determined by methods well-known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 0.5 to 500 µg purified protein can be given.

The present invention is also directed to a vaccine in which an antigenic protein, or antigenic fragment thereof, is delivered or administered in the form of a polynucleotide encoding the protein or fragment (i.e., a DNA vaccine). In DNA vaccination, the patient is administered a polynucleotide encoding a antigenic protein that is then transcribed, translated and expressed in some form to produce strong, long-lived humoral and cell-mediated immune responses to the antigen. The polynucleotide can be administered using viral vectors or other vectors, such as liposomes, and can be combined with a acceptable carrier.

In addition, the proteins of the present invention can be used as antigens to stimulate the production of antibodies for use in passive immunotherapy, for use as diagnostic reagents, and for use as reagents in other processes such as affinity chromatography.

The present invention also embraces a method of using the presently disclosed anti-MAP vaccine as a means of immunizing animals, especially mammals, most particularly humans, against a MAP infection. In accordance with such a method, a MAP vaccine containing at least one MAP antigen, or attenuated or killed MAP is administered to a human subject in an amount effective to stimulate a measurable immune response. A measurable immune response can include a humoral response (e.g., production of antibodies to a particular antigen) or cell-mediate immune response (e.g., elicitation of a T cell response as determined by the production of cytokines such as IFN-gamma or IL-10).

In so far as the vaccine disclosed herein can be used to immunize a human against a MAP infection, the present invention also provides for a method of preventing or treating a MAP infection, as well as a human disease associated with a MAP infection. Such methods involve administering to a human subject, a vaccine containing at least one MAP antigen, or attenuated or killed MAP, as disclosed herein, in an amount effective to prevent or attenuate said MAP infection or symptoms of the MAP-associated disease. In using the methods of the invention, the disease to be prevented or treated is desirably ulcerative colitis, irritable bowel syndrome, Crohn's Disease, Multiple Sclerosis, Alzheimer's Disease, sarcoidosis, ankylosing spondylitis, psoriasis, psoriatic arthritis or rheumatoid arthritis.

The invention is described in greater detail by the following non-limiting examples.

Example 1

Anti-MAP Vaccine

Mice (10 per group, e.g., wild-type or IL-18 deficient mice (Momotani, et al. (2002) *Proc. 7$^{th}$ Intl. Coll. Paratuberculosis,* Juste (ed)) are immunized intraperitoneally (i.p.) with either AhpC or AhpD protein (15 µg in 50 µl PBS (phosphate-buffered saline) emulsified in 50 µl complete Freund's adjuvant (CFA)). A group of 10 mice are sham-immunized with PBS and CFA only.

A second immunization of 15 µg protein with incomplete Freund's adjuvant (IFA) is administered 3 weeks later (with the sham-immunized group receiving PBS and IFA).

Blood is drawn at weeks 5 and 7. Sera from each group are pooled for analysis of anti-AhpC and anti-AhpD antibody by ELISA. Mice are challenged at week 8 by intraperitoneal injection of MAP. Mice are monitored for signs and symptoms of disease.

Data will indicate that immunization of mice with either recombinant AhpC or AhpD proteins elicits a response capable of protecting against MAP infection.

Example 2

Immunogenicity of Anti-MAP Vaccine in Humans

Sera from patients with culture-proven MAP infection are used in western blot analysis containing recombinant AhpC or AhpD protein.

The results of this analysis will demonstrate that sera from patients with MAP infections exhibit reactivity with either AhpC or AhpD, thereby indicating that AhpC and AhpD are recognized by the human immune system and suggest that antibodies able to bind the AhpC or AhpD protein can be produced during natural MAP infection in humans. Further, this data provides evidence that AhpC and AhpD are expressed in vivo by MAP during infection, and thus can be available as targets for immunoprophylaxis, immunotherapy, or to provide immune responses in subjects vaccinated with these proteins.

What is claimed is:

1. A method for immunizing a human against a MAP infection comprising administering to a human subject a vaccine containing at least one MAP antigen, or killed MAP thereby immunizing the human against a MAP infection, wherein the killed MAP is cell wall-competent or cell wall-deficient and said MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, or AhpC antigen.

2. A method for preventing a human disease associated with a MAP infection comprising administering to a human subject a vaccine containing at least one MAP antigen, or killed MAP thereby conferring immunity to the MAP organisms and preventing a human disease associated with a MAP infection, wherein the killed MAP is cell wall-competent or cell wall-deficient and said MAP antigen is GroES, AhpD, 32 kDa antigen, 34 kDa antigen, 34.5 kDa antigen, 35 kDa antigen, 36 kDa antigen, 42 kDa antigen, 44.3 kDa antigen, or AhpC antigen.

* * * * *